United States Patent [19]

Kim

[11] Patent Number: 5,227,407
[45] Date of Patent: Jul. 13, 1993

[54] WATER ADDITION FOR INCREASED CO/$H_2$ HYDROCARBON SYNTHESIS ACTIVITY OVER CATALYSTS COMPRISING COBALT, RUTHENIUM AND MIXTURES THEREOF WHICH MAY INCLUDE A PROMOTER METAL

[75] Inventor: Chang J. Kim, Seoul, Rep. of Korea

[73] Assignee: Exxon Research and Engineering Company, Florham Park, N.J.

[21] Appl. No.: 848,882

[22] Filed: Mar. 11, 1992

Related U.S. Application Data

[63] Continuation-in-part of Ser. No. 676,640, Mar. 28, 1991, abandoned, which is a continuation-in-part of Ser. No. 417,384, Oct. 5, 1989, abandoned, which is a continuation-in-part of Ser. No. 237,355, Aug. 29, 1988, abandoned, which is a continuation-in-part of Ser. No. 84,629, Aug. 11, 1987, abandoned, which is a continuation-in-part of Ser. No. 814,679, Dec. 30, 1985, abandoned.

[51] Int. Cl.$^5$ .................................................. C07C 1/04
[52] U.S. Cl. ..................................... 518/700; 518/711; 518/715
[58] Field of Search ........................ 518/711, 715, 700

[56] References Cited

U.S. PATENT DOCUMENTS

| | | |
|---|---|---|
| 2,475,214 | 7/1949 | Barr . |
| 2,497,964 | 2/1950 | Simpson . |
| 2,594,301 | 4/1952 | Eastman et al. . |
| 3,927,999 | 12/1975 | Child et al. . |
| 4,385,193 | 5/1983 | Bijwaard et al. . |
| 4,568,663 | 2/1986 | Mauldin . |
| 4,595,703 | 6/1986 | Payne et al. . |
| 4,628,133 | 12/1986 | Minderhoud . |
| 4,670,475 | 6/1987 | Mauldin . |

FOREIGN PATENT DOCUMENTS

| | | |
|---|---|---|
| 530932 | 9/1956 | Canada . |
| 0109702 | 5/1984 | European Pat. Off. . |
| 0216967 | 4/1987 | European Pat. Off. . |
| 0266898 | 5/1988 | European Pat. Off. . |
| 487379 | 12/1929 | Fed. Rep. of Germany . |
| 716853 | 1/1942 | Fed. Rep. of Germany . |
| 2388782 | 11/1978 | France . |
| 77441 | 10/1954 | Netherlands . |

OTHER PUBLICATIONS

Kikuchi, et al. Applied Catalysis 10 (1984) 251–260.

*Primary Examiner*—Howard T. Mars
*Attorney, Agent, or Firm*—Jay Simon; Estelle C. Bakun

[57] ABSTRACT

The addition of water into a Fischer-Tropsch hydrocarbon synthesis reaction zone employing passing a CO and $H_2$ feed mixture over a catalyst comprising cobalt, ruthenium and mixtures thereof preferably on a titania support and which may include a promoter metal, that results in 90% CO conversion to hydrocarbons and increased $C_5+$ hydrocarbon selectivity, along with a decrease in methane production.

10 Claims, No Drawings

WATER ADDITION FOR INCREASED CO/H₂ HYDROCARBON SYNTHESIS ACTIVITY OVER CATALYSTS COMPRISING COBALT, RUTHENIUM AND MIXTURES THEREOF WHICH MAY INCLUDE A PROMOTER METAL

CROSS REFERENCE TO RELATED APPLICATION

This is a continuation-in-part of copending U.S. Ser. No. 676,640 filed March 28, 1991 (abandoned Mar. 24, 1992), which is a continuation-in-part of U.S. Ser. No. 417,384, filed Oct. 5, 1989 (abandoned Mar. 28, 1991), which is a continuation-in-part of U.S. Ser. No. 237,355, filed Aug. 29, 1988 (abandoned Oct. 5, 1989), which is a continuation-in-part of U.S. Ser. No. 084,629, filed Aug. 11, 1987 (abandoned Aug. 29, 1988), which is a continuation-in-part of U.S. Ser. No. 814,679 filed Dec. 30, 1985 (abandoned Aug. 17, 1987), based on U.S. Ser. No. 313,565, filed Feb. 21, 1989 (abandoned Oct. 5, 1989), which is a Rule 60 continuation of U.S. Ser. No. 115,971, filed Nov. 2, 1987 (abandoned Feb. 21, 1989), based on U.S. Ser. No. 541,659, filed June 21, 1990 (abandoned Apr. 15, 1991), which is a Rule 60 continuation of U.S. Ser. No. 185,953, filed Apr. 25, 1988 (abandoned Jan. 31, 1991).

BACKGROUND OF THE INVENTION

This invention relates to a water addition process for increasing the activity of a Fischer-Tropsch, fixed bed or slurry bed, hydrocarbon synthesis reaction over a catalyst comprising metals selected from ruthenium, cobalt and mixtures thereof. The catalyst preferably will be supported on a support containing titania. However, where cobalt metal is used, the catalyst may be in bulk form. More particularly, this invention relates to increasing catalyst activity by decreasing the methane make, increasing the CO conversion and increasing $C_5+$ hydrocarbon selectivity of a Fischer-Tropsch hydrocarbon synthesis process which comprises feeding a mixture of $H_2$, CO and $H_2O$ into a reaction zone containing a catalyst comprising metals selected from ruthenium, cobalt and mixtures thereof in the reduced, metallic form wherein said mixture contacts said catalyst at elevated temperature for a time sufficient to convert at least a portion of said feed to $C_5+$ hydrocarbons.

BACKGROUND OF THE DISCLOSURE

The production of hydrocarbons from mixtures of $H_2$ and CO via the Fischer-Tropsch process is well known to those skilled in the art. As opposed to the well-known "methanization" process which produces methane as synthetic natural gas from mixtures of $H_2$ and CO, the Fischer-Tropsch process is more generally aimed at producing higher value products such as chemical feedstocks and liquid fuels. Thus, high methane make is undesirable in Fischer-Tropsch synthesis processes because it is a relatively low value product which is formed at the expense of more desirable products. It is also uneconomical to try to convert the so-formed methane back into a CO and $H_2$ mixture and recycle it back into the reactor.

Methane make in Fischer-Tropsch reactions is often expressed by a term known as methane selectivity. Methane selectivity can be defined by either of two methods. They are: (a) mole % $CH_4$ produced based on the amount of CO consumed or (b) weight % of $CH_4$ produced based on total hydrocarbon products formed.

Many different catalysts and processes have been disclosed for Fischer-Tropsch synthesis, some of which have extremely high methane make.

Cobalt Catalysts

Thus, U.S. Pat. No. 4,077,995 discloses synthesis of $C_1$–$C_4$ aliphatic hydrocarbons over a catalyst comprising a sulfided mixture of CoO, $Al_2O_3$ and ZnO while U.S. Pat. No. 4,039,302 discloses $C_1$–$C_3$ hydrocarbon production using a mixture of the oxides of Co, Al, Zn and Mo. U.S. Pat. No. 4,151,190 discloses producing $C_2$–$C_4$ hydrocarbons from mixtures of CO and $H_2$ using a supported catalyst comprising a metal oxide or sulfide of Mo, W. Re, Ru, Ni or Pt plus an alkali or alkaline earth metal, with Mo-K on carbon being preferred. U.S. Pat. Nos. 4,243,553 and 4,243,554 disclose $MoS_2$ as a Fischer-Tropsch catalyst. Many other catalysts are known to be useful for Fischer-Tropsch synthesis employing metals such as iron, copper, titania, etc. These are known to those skilled in the art.

The type of catalyst used and process conditions employed have an important bearing on $CH_4$ selectivity. For example, nickel gives a high $CH_4$ selectivity and is used mainly as a methanization catalyst. Methane selectivity usually increases with increasing temperature, decreasing pressure and increasing the $H_2/CO$ ratio of the feed. Accordingly, process conditions are selected so as to minimize $CH_4$ selectivity while maintaining a relatively high reaction rate as is well known to those skilled in the art.

It is known that $CH_4$ selectivity is influenced by the choice of promoter and support, such as alkali metal promoters reducing $CH_4$ selectivities of iron catalysts. It is also known in the art that noble metals such as ruthenium supported on inorganic refractory oxide supports exhibit superior hydrocarbon synthesis characteristics with relatively low methane production. Thus, U.S. Pat. No. 4,088,671 suggests minimizing methane production by using a small amount of Ru on a cobalt catalyst. Examples of supported ruthenium catalysts suitable for hydrocarbon synthesis via Fischer-Tropsch reactions are disclosed in U.S. Pat. Nos. 4,042,614 and 4,171,320. It is also known that the type of support used also influences methane production. In the case of supported ruthenium catalysts, the use of a titania or titania containing support will result in lower methane production than, for example a silica, alumina or manganese oxide support.

European patent application 83201557.2 relates to a Fischer-Tropsch hydrocarbon synthesis process employing, as a catalyst, cobalt supported on silica promoted with zirconium, titanium or chromium wherein the cobalt is deposited on the silica carrier by a kneading process. In this process, 10 to 40 volume percent steam is added to the feed, based on the $H_2/CO/H_2O$ mixture. The amount of cobalt present in the catalyst is 10–40 pbw based on 100 pbw of silica. In the examples, very little enhancement in either CO conversion of $C_3+$ selectivity is shown as a result of the water addition to the feed. U.K. patent application 2,146,350A relates to a Fischer-Tropsch hydrocarbon synthesis process employing a similar catalyst, followed by a hydrocracking process wherein the Fischer-Tropsch products are hydrocracked over a noble metal catalyst. The same type of catalyst is also used in the Fischer- Tropsch processes described in U.K. patent application nos. 2,149,812A and 2,149,813A.

U.S. Pat. No. 4,628,133 discloses the use of steam with a cobalt/silica catalyst and reports that activity decreased with the addition of water while selectivity to $C_9+$ products increased. Thus, the overall yield of valuable products decreased but the selectivity to certain products was enhanced. In Satterfield et al., AIChE Journal, #3338, p.E7, July 1985, water addition over iron based catalysts again showed decreased activity although the effect was reversible upon removal of the water.

U.S. Pat. No. 3,927,999 relates to a process for producing a methane rich fuel gas containing 70 to 98 mole % methane by contacting a mixture of $H_2$, CO and $H_2O$ with a suitable catalyst at elevated temperature. This invention is based on the discovery that the methane content of the product gas from the methanator is maximized by adjusting the mole % $H_2O$ in the synthesis gas feed to a critical value in the range of 1 to 3, while maintaining the $H_2/CO$ mole ratio of the synthesis gas feed to a critical value in the range of about 1 to 1.15. The feed gas may also contain methane. Group VIII transition metals such as iron, nickel and cobalt are suggested as suitable catalysts, but only nickel on alumina is actually used. Example 1 shows the production of a fuel gas containing 96.4 mole $CH_4$ from a feed gas containing 48.1 mole % $CH_4$ over a catalyst containing nickel, thoria, magnesia and kieselguhr.

U.S. Pat. No. 2,479,439 relates to a process for alternately increasing the activity of an alkali metal promoted, powdered iron catalyst or decreasing the coke buildup thereon, or accomplishing both simultaneously by passing an aqueous solution of alkali metal salt, such as KF, into the hydrocarbon synthesis reaction zone to contact the iron catalyst. The presence of the water is said to remove carbon from the iron catalyst. U.S. Pat. No. 2,539,847 relates to a Fischer-Tropsch hydrocarbon synthesis process employing a catalyst consisting of thoria promoted cobalt supported on bentonite. U.S. Pat. No. 4,568,663 relates to a Fischer-Tropsch hydrocarbon synthesis process employing a rhenium cobalt on titania catalyst.

The Fischer-Tropsch (FT) process, the process to which this invention relates, must also be distinguished from the well known Kolbel-Engelhardt (KE) process (described, for example, in Canadian Patent No. 530,932). The FT process may be described by equation (1), the KE process by equation (2).

$$2nH_2 + nCO \rightarrow -(CH_2)_n- + nH_2O \quad (1)$$

$$nH_2O + 3nCO \rightarrow -(CH_2)_n- + 2nCO_2 \quad (2)$$

The two processes may appear similar in that they yield similar products and can employ Group VIII metals as catalysts. The reactions are not similar because their reaction paths differ. In FT synthesis, in the absence of substantial water gas shift, at least about 90% of the CO is converted to hydrocarbon products. However, in KE, up to only about 33% of the CO is converted to hydrocarbon products. FT yields $H_2O$ as a product while KE consumes $H_2O$ as a reactant and generates $CO_2$ as a by-product. The reactions can be distinguished in that in FT there is no net consumption of $H_2O$, whereas in KE there is net consumption of $H_2O$. Even if hydrogen is added to the reaction mixture for KE, water will be consumed.

Equation two indicates that for every three moles of carbon monoxide consumed, two moles of carbon dioxide are necessarily produced. If carbon monoxide were to be 100% converted, two-thirds would be converted to carbon dioxide. This ratio holds throughout the KE synthesis. Therefore:

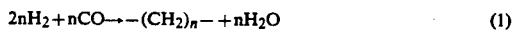
Moles of CO converted $\times \frac{2}{3}$ = Mole of CO converted to $CO_2$

Moles of CO converted $\times \frac{1}{3}$ = Moles of CO converted to hydrocarbon The present invention teaches the nonwater gas shift Fischer-Tropsch hydrocarbon synthesis using a noniron catalyst. Under ideal conditions, for every 100 moles of carbon monoxide converted, 0 moles of carbon dioxide are produced. Clearly the present invention is different from the KE synthesis.

A further differentiation of the KE process is shown in Chaffee, et al., Applied Catalysis, 19, p. 419–422 (1985) where the KE reaction produces relatively high levels of aromatic products. The process of this invention by contrast produces substantially all paraffins.

Ruthenium catalysts for use in Fischer-Tropsch synthesis were first discovered by Pichler (see H. Pichler, *Brennstoff-Chem.* 19, 226 (1938) and H. Pichler, and H. Bufflet, *Brennstoff-Chem.* 21, 247, 273, 285 (1940) that Ru catalyst can produce $H_2/CO$ mixtures at low temperature and high pressures, very high molecular weight waxes of about MW 1000 and above, i.e., polymethylenes, having melting points of 100° C. and above. Karn, et al., *I&EC Product Res. & Devel.* 4, 265 (1965) describe the reactivity of ruthenium on alumina catalysts in producing hydrocarbons ranging from $C_1$–$C_{30}+$ including runs made at 21.4 atmospheres pressure, 300/hr. space velocity, temperature of 220°–240° C. and $H_2/CO$ molar ratios of 1 to 4 resulting in % CO conversions of 46-82%. U.K. Patent Application 2,024,246A describes a hydrocarbon synthesis process for hydrocarbons in the $C_5$–$C_{12}$ range, in which mixtures of $H_2CO$ are contacted with a supported ruthenium catalyst, preferably on alumina at elevated temperature. A criticality of the process is described wherein the outlet CO partial pressure must be not less than 0.8 atmospheres at a process temperature of about 500°–525° K. and not less than 3.0 atmospheres in the temperature range of 525°–550° K.

R. J. Madon in *J. of Catalysis* 57, 183–186 (1979) describes the $C_5$–$C_{20}$ production of hydrocarbons in Fischer-Tropsch processes utilizing ruthenium on alumina catalyst.

U.S. Pat. Nos. 4,042,614, 4,042,615 and 4,116,994 to Vannice and Garten disclose ruthenium, nickel and rhodium, respectively, supported on titania and titania-containing supports as Fischer-Tropsch catalysts for producing hydrocarbons from mixtures of CO and $H_2$. Ko and Garten in *Ethane Hydrogenolysis Studies of Ti-$O_2$-Supported Group VIII Metal Catalysts*, J. Catalysis, v. 68, pp. 233–236 (1981) disclose each and every one of the Group VIII metals on both silica and titania supports as ethane hydrogenolysis catalysts. Vannice, in a 1982 article titled *Titania-Supported Metals as CO Hydrogenation Catalysts*, J. Catalysis v. 74, pp. 199–202 (1982), discloses each one of the Group VIII metals, except osmium, supported on a titania support for Fischer-Tropsch synthesis of hydrocarbons. In this article, Vannice states that rhodium and ruthenium on titania did not have as high a CO conversion activity as nickel on titania, but produced more useful hydrocarbons and less methane make than nickel on titania.

Wells, et al., in a 1982 article titled "Supports Effects in the Ruthenium Catalyzed Hydrogenation of Carbon Monoxide," appearing on pages 247-254 of *Metal-Supported and Metal-Addition Effects in Catalysis*, Imelik, et al. (Ed.), Elsevier 1982, also disclose ruthenium supported on titania as a Fischer-Tropsch catalyst. This article compares both the CO conversion activity and the $CH_4$ production activity of ruthenium on both anatase and rutile containing titania. Wells et al. found that the CO conversion activity was substantially greater for ruthenium on anatase titania than for ruthenium on rutile titania. The methane activities were fairly similar. Another article on pages 337-348 of the same book by Reymond, et al., titled *Influence of the Support or of an Additive on the Catalytic Activity in the Hydrocondensation of Carbon Monoxide by Iron Catalysts* compares iron on various support materials as Fischer-Tropsch catalysts. FIG. 2 of this article compares the activities, in terms of methane production, or iron on both anatase is shown to be substantially greater than rutile.

U.S. Pat. No. 4,477,595 to R. J. Madon discloses a Fischer-Tropsch process for selectively producing paraffinic hydrocarbons employing a catalyst comprising ruthenium supported on an inorganic refractory metal oxide support, preferably wherein the support material includes titania or various titanates and wherein the ruthenium metal loading on the catalyst may range from 0.01 to 15 wt. %. S. R. Morris, et al., in "Metal-Support and Metal-Additive Effects in Catalysis," Ed. B. Imelik et al., Elsevier, 1982 disclose a ruthenium supported on titania catalyst used in Fischer-Tropsch catalysis wherein the amount of the supported ruthenium range from 2 to 17 wt. %. This article discloses no trend in $CH_4$ selectivity or paraffin olefin ratios as a function of the Ru loading level on the catalyst.

C. H. Yang, et al., in "Physical Effects on Fischer-Tropsch Synthesis Over Composite Ru Catalysts," *Canadian J. Chem. Eng.*, 61, 213-217 (1983) employed a mixture of catalysts for Fischer-Tropsch synthesis. The catalysts both employed 6.5 wt. % ruthenium. In one case the support was titania and in the other catalyst the support was a mixture of titania and silica in a 1:4 volume ratio. The minimum methane make was reported as being about 20%. Dautzenberg, et al., "Pulse-Technique Analysis of the Kinetics of the Fischer-Tropsch Reaction," J. of Catalysis, 50, 8-14 (1977) employed ruthenium supported on alumina as a catalyst. After hydrogen reduction at 350° C., the catalyst was then contacted with a mixture of $CO/H_2$ at 210° C. from 4-12 minutes followed by 14 minutes on pure $H_2$, followed by 4 minutes with $CO/H_2$. The object was to observe product formation under such short exposure to $CO/H_2$ reagents.

Toshiaki-Mori, et al., in "Promoting Effect of V, Mo, W, and Re on the Rate of C-O Bond Dissociation of Adsorbed CO in Methanation on $Ru/A1203$," *J. Chem. Society Commun.* 678-679 (1984) disclose promoting $Ru/A1203$ catalysts with various metals at a Ru loading of 0.5 wt. %. This was also a pulse technique and not a steady-state reaction and the product was almost all methane.

Stowe, et al., in "Optimize Syngas to Naphtha Over Ruthenium Catalysts," *Hydrocarbon Processing*, 95-100 (June, 1984) disclose Ru on various aluminas at a Ru loading level of 0.5, 1.0 and 2.0 wt. %. E. Kikuchi, et al., in "Fischer-Tropsch Synthesis Over Titania-Supported Ruthenium Catalysts," *Applied Catalysis*, 10, pp. 251-260 (Elsevier, 1984) employed ruthenium on both titania and alumina supports at a ruthenium loading range from 0.5 to 2.0 wt. %. In all cases, their data shows a minimum methane make of 16 wt. % with a titania support and 25 wt. % with an alumina support.

There exists a need in the art for Fischer-Tropsch processes useful for the conversion of mixtures of CO and hydrogen to $C_5+$ hydrocarbons at high CO conversion levels, and high hydrocarbon yields, with relatively low methane make.

SUMMARY OF THE INVENTION

It has now been discovered that in a fixed or slurry bed, nonrecirculating Fischer-Tropsch hydrocarbon synthesis reaction for producing $C_5+$ hydrocarbons from a gaseous feed mixture of $H_2$ and CO in the presence of a catalyst comprising bulk cobalt or metals selected from cobalt, ruthenium and mixtures thereof, mounted on a titania support, one can increase both the CO conversion activity and the $C_5+$ hydrocarbon selectivity and, at the same time, decrease the methane make by adding $H_2O$ to the reaction zone. The present invention relates to a nonrecirculating Fischer-Tropsch process for synthesizing $C_5+$ hydrocarbons by introducing into a catalytic reaction zone a feed mixture of CO and $H_2$ and added $H_2O$ wherein said CO and $H_2$ feed mixture react with a catalyst comprising metals selected from ruthenium, cobalt and mixtures thereof, where the catalyst has a titania containing support. Where cobalt metal is used, the catalyst may be in bulk form. The reaction is conducted at elevated temperatures for a time sufficient to convert at least a portion of said feed to $C_5+$ hydrocarbons. By cofeeding $H_2O$ into the reaction zone, along with the $H_2$ and CO feed mixture, it has been found that $C_5+$ hydrocarbon production is increased, CO conversion is increased such that at least about 90% of the CO is converted to hydrocarbon products and $CH_4$ production is decreased. The increase in activity and selectivity is effected in the substantial absence of $CO_2$ formation (less than about 2% based on feed).

In one aspect of the invention, the catalyst may be cobalt alone as in the reduced, metallic form, preferably a high surface area cobalt such as cobalt black or a more conventional preparation such as cobalt on titania.

The $H_2O$ that is added to the reaction zone may be in the form of steam or moisture or a suitable $H_2O$ precursor, such as $C_1$-$C_6$ alcohols, for forming $H_2O$ in-situ in the reaction zone. It is essential to the understanding of the process of this invention that the $H_2O$ introduced into the reaction zone is external $H_2O$ that $H_2O$ which is formed in-situ in the reaction zone as a consequence of the Fischer-Tropsch hydrocarbon synthesis reaction from the $H_2$ and CO. It has also been found that the process of this invention improves with increasing pressure in the reaction zone and with decreasing CO conversion.

The addition of water to the reaction process does not aid all catalysts. In fact, water addition is catalyst specific. For example, water addition has no advantageous effect on iron based catalysts and shows a selectivity advantage but an activity debit with cobalt/silica catalysts. By contrast, for example, catalysts such as cobalt black and cobalt on titania show advantageous results for water addition for both activity and selectivity, particularly with regard to $C_{10}+$ paraffins.

In a preferred embodiment of the invention, the synthesis gas feed, carbon monoxide and hydrogen is substantially free of, and preferably completely (except for trace amounts) free of methane or other light hydrocarbons. The hydrocarbon free synthesis gas feed is easily accomplished in a once-through system where there is no recycle of unconverted hydrogen and carbon monoxide (along with undesirable light hydrocarbons) directly to the hydrocarbon synthesis reaction zone. Preferably, the synthesis gas feed contains only $H_2$, CO and water and is substantially free of light hydrocarbons, e.g., methane. Allowable limits on light hydrocarbons in the synthesis gas feed are no more than about 1 vol. % and preferably less than about 0.5 vol.

DETAILED DESCRIPTION

The process of the present invention resides in adding, to the Fischer-Tropsch reaction zone, $H_2O$ or a suitable $H_2O$ precursor such as an alcohol. The amount of $H_2O$ added to the reaction zone will range from about 1-70 volume % of the total feed mixture of $H_2O$, CO and $H_2$ and, preferably, from about 5-30 volume As the extent of CO conversion increases, the amount of water produced in-situ in the reaction zone increases and, concomitantly the beneficial effect of introducing additional water into the reaction zone to increase CO conversion, reduce $CH_4$ selectivity and increase $C_{5+}$ hydrocarbons selectivity decreases. Thus, in some cases, it may be advantageous to practice the process of this invention at CO conversion levels below about 60 percent. That is, below about 60% per pass, reaction zone, or stage. As the pressure in the reaction zone increases, the beneficial effect of the process of this invention of adding water to the reaction zone increases with respect to increasing CO conversion activity, decreased $CH_4$ selectivity and increased $C_{5+}$ hydrocarbon selectivity. At relatively low pressures in the reaction zone (i.e., less than about 1 atmosphere), little effect will be seen in increased conversion activity, etc. by adding $H_2O$ to the reaction zone. Thus, the process of this invention will be operated at a pressure above about one atmosphere. In general the pressure will range from about 1-50 atmospheres, and more preferably 5-30 atmospheres.

In the process of this invention, the addition of $H_2O$ enhances the formation of $C_{5+}$ hydrocarbons, particularly $C_{10+}$ hydrocarbons and reduces $CH_4$ make in a uni-directional or linear fashion. It has also been found that the rate of the Fischer-Tropsch reaction employing the process of this invention increases with increasing partial pressure of $H_2O$ at any fixed total pressure in the reaction zone, up to a point, after which point the rate slowly goes down with continually increasing $H_2O$ partial pressure.

In general, the Fischer-Tropsch hydrocarbon synthesis reaction process of this invention is carried out at a $H_2$:CO mole ratio of greater than about 0.5, and preferably the $H_2$:CO mole ratio ranges from about 0.5 to about 6, more preferably from about 0.5 to about 3, and still more preferably from about 1.50 to about 2.1 at gas hourly space velocities ranging from about 100 V/Hr/V to about 5000 V/Hr/V, preferably from about 300 V/Hr/V to about 1500 V/Hr/V, at temperatures ranging from about 150 C to about 300° C., preferably from about 180° C. to about 240° C., and pressures above about 1 atm, preferably ranging from about 1 atm to about 50 atm, more preferably from about 5 atm to about 40 atm and still more preferably from about 5-30 atmospheres.

As previously stated, the hydrocarbon synthesis process of this invention employs a catalyst comprising cobalt in its reduced, metallic-form, preferably a high surface area cobalt such as cobalt black. The cobalt may be in the form of a finely divided powder, or granules which may be mixed with a suitable diluent to aid in heat transfer and removal from the reaction zone. The cobalt may be supported on a suitable support material, such as cobalt plated on carrier metal. The cobalt in bulk form, or plated, explosion-coated, etc. may also be in the form of various high surface area shapes such as spirals, metal wool, honeycomb configurations, etc., the choice being left to the practitioner.

The hydrocarbon synthesis process of this invention may also employ a catalyst comprising ruthenium supported on $TiO_2$. This catalyst will also be a particulate catalyst composition containing a catalytically active amount of ruthenium. In general, the ruthenium metal loading on the titania support will generally range from about 0.1 to 20 wt. % ruthenium metal and preferably from about 0.1 to 10 wt. % based on the total catalyst weight. These percentages refer to the ruthenium metal in the reduced metal form.

When supported catalysts are employed, for example, cobalt on a support such as titania, the improvement in the process from the addition of water is apparent only with supports of a relatively low surface area. Thus, supported cobalt catalyst preferably have a surface area of less than about 40 square meters per gram of catalyst (BET). The preferred support, therefore, is titania which has a surface area of less than about 40 m$^2$/gm. As previously mentioned, other supports do not show the combined result of increased activity and increased selectivity with the addition of $H_2O$.

A preferred titania support is one that is primarily $TiO_2$, preferably greater than about 50% titania, more preferably at least about 75% titania, and still more preferably substantially completely $TiO_2$, and has a rutile content of at least 40 wt. %. The rutile anatase weight ratio is preferably about 3:2 and is determined by ASTM D3720-78: Standard Test Method for Ratio of Anatase to Rutile in Titanium Dioxide Pigments by Use of X ray Diffraction.

The titania supported catalyst can be prepared by a variety of known techniques, e.g., by gelation, or cogelation. Suitably, however, the cobalt can be deposited on a previously pilled, pelleted, beaded, extruded, or sieved support material by the impregnation method. In preparing a cobalt based catalyst, the cobalt is deposited from solution on the support in preselected amounts to provide the desired absolute amounts. When promoter metals are employed, such as rhenium and hafnium and mixtures thereof, the metal amounts deposited should also reflect the weight ratios of each metal. Preferably the promoter will comprise rhenium alone.

The promoter, if used, will be added to the catalyst in an amount to form a catalyst having a promoter:cobalt weight ratio greater than about 0.010:1, preferably from about 0.025:1 to about 0.10:1. In terms of absolute concentrations, from about 0.05 percent to about 3 percent of rhenium, preferably from about 0.15 percent to about 1 percent of promoter, based on the total weight of the catalyst composition (dry basis), is dispersed with the catalytically active amount of cobalt on a titania support. In terms of absolute concentrations, cobalt is present in the composition in amounts ranging from about 2 percent to about 25 percent, preferably from about 5 percent to about 15 percent, based on the total weight of the catalyst composition (dry basis), and sufficient promoter, such as rhenium, is added to form a catalyst having a weight ratio of rhenium:cobalt greater than about 0.010:1, preferably from about 0.025:1 to about 0.10:1, based on the total weight of the cobalt and rhenium contained in the catalyst composition (dry basis). The absolute concentration of each metal will, of course, be preselected to provide the desired ratio of rhenium:cobalt as heretofore expressed.

The catalysts useful in this invention are prepared by depositing the metal or metal precursor component onto the support material from a precursor solution using any of the well-known techniques such as incipient wetness, multiple impregnation, pore-filing, etc. the choice being left to the convenience of the practitioner. Suitably, one metal can be first composited with the support, and then the other; or both may be added simultaneously. The amount of impregnation solution used should be sufficient to completely immerse the titania, usually within the range from about 1 to 20 times the carrier by volume, depending on the metal, or metals, concentration in the impregnation solution. The impregnation treatment can be carried out under a wide range of conditions including ambient or elevated temperatures.

The catalyst, after impregnation, is dried to remove solvent and/or water by heating. In the case of cobalt metal, the drying temperature is above about 25° C., preferably between about 65° C. and 150° C., in the presence of nitrogen or oxygen, or both, in an air stream or under vacuum. In the case of ruthenium metal, drying is performed at a relatively low temperature of less than about 100° C. and slowly raising the temperature to between 200° and 500° C. Drying is conducted for a time sufficient to reduce the metal precursor on the support material. The metal or metals contained on the catalyst can then be reduced.

Reduction is performed by contact of the catalyst with hydrogen or a hydrogen containing gas stream at temperatures ranging from about 150° C. to about 565° C. for periods ranging from about 0.5 to about 24 hours at from about 100 kPa to about 4000 kPa, depending on the nature of the metal precursor and impregnation or deposition technique employed and the extent of catalytic metal loading desired for the final catalyst. A gas containing hydrogen and inert components, or a gas containing hydrogen and carbon monoxide in admixture are satisfactory for use in carrying out the reduction.

Suitably, the cobalt on a titania support is present in a catalytically active amount, e.g., 2 to about 25 wt. %, preferably 5 to 20 Wt. % (dry basis). Promoter metals may be present in amounts to form a weight ratio of promoter:cobalt greater than about 0.01 to 1; preferably 0.025 to about 0.1 to 1 based on total weight of cobalt and promoter.

The following examples will serve to illustrate the invention.

EXAMPLES

Example 1

Bulk Co

A bulk cobalt catalyst, designated as a cobalt black catalyst, was prepared by a conventional method known in the art, i.e., adding a stoichiometric amount of ammonium carbonate (as an aqueous solution) to an aqueous solution of cobalt nitrate, filtering the precipitate, washing the filtered solid with deionized water, drying at 120° C., and calcining at 500° C. in air for 5 hours. The resulting material showed an X ray diffraction patter of $Co_3O_4$ which, when reduced at 450° C. in a $H_2$ stream, produced a cobalt black catalyst having a surface area of 7.7 $m^2$/gr.

The performance test of this catalyst was carried out by charging an intimate mixture of the $Co_3O_4$ powder (6.8 grams) and a diluent (quartz powder, 80–140 mesh, 18 grams) into a down-flow fixed bed reactor made of $\frac{1}{2}$" OD stainless steel tube with a concentric $\frac{1}{8}$" OD thermocouple well. When reduced, 6.8 grams of $Co_3O_4$ will yield 5.0 grams of cobalt black. The use of diluent and an aluminum block jacket fitted tightly around the reactor minimized uneven temperature profile along the bed. The $Co_3O_4$ was then reduced in-situ in the reactor in a flowing $H_2$ stream (200 cc/m, 1 atm) overnight at 450° C., cooled to 175° C. and then pressurized to 20 atm using a pre-mixed gas composed of 63.1% $H_2$, 33.0% CO and 3.9% $N_2$. At pressure and at a preset flow rate, the temperature was raised to 200° C. over a period of one hour and then data acquisition was initiated. The rate of CO conversion and the rates of various hydrocarbon products formation were monitored using two on-line GC's. The data taken after 70 hour on-stream-time are shown in Table 1.

TABLE 1

EFFECTS OF EXTERNAL $H_2O$ ADDITION ON ACTIVITY SELECTIVITIES OF Co BLACK

Temperature = 200° C.
Feed Gas Composition = 63.1% $H_2$/33.0% CO/3.9% $N_2$
SV = 3600 $Scm^3$/g hour (calculated for $H_2$ and CO)*[1]

| | Run 1 | Run 2 | Run 3 | Run 4 |
|---|---|---|---|---|
| % $H_2O$ Added*[2] | 0 | 12.5 | 27.7 | 50.0 |
| Total Pressure, atm | 20.7 | 21.6 | 24.9 | 28.6 |
| $PH_2$ + Pco, atm | 20.0 | 18.7 | 18.9 | 18.6 |
| $PH_2O$, atm | 0 | 2.3 | 5.2 | 9.3 |
| % CO Conv. | 12.1 | 27.3 | 28.7 | 18.8 |
| $CH_4$ Select*[3] | 10.5 | 7.1 | 5.8 | 4.0 |
| $CO_2$ Select*[3] | 0.27 | 0.21 | 0.34 | |
| Hydrocarbon Product Distribution, wt. % | | | | |
| $CH_4$ | 11.5 | 8.1 | 6.7 | 4.6 |
| $C_2$–$C_4$ | 15.6 | 8.7 | 7.8 | 8.6 |
| $C_5$–$C_9$ | 17.4 | 9.5 | 9.0 | 9.7 |
| $C_{10}$+ | 55.5 | 73.7 | 76.5 | 77.1 |
| $C_{10}$–$C_{20}$ | 21.7 | 17.0 | | |
| $C_{21}$–$C_{30}$ | 21.7 | 13.8 | | |
| $C_{31}$–$C_{40}$ | 6.9 | 11.1 | | |
| $C_{41}$–$C_{50}$ | 4.7 | 8.1 | | |
| $C_{51}$+ | 11.8 | 23.7 | | |

*[1] cc of $H_2$ and CO measured at 1 atm, 22° C. per gram of catalyst per hour
*[2] Moles of $H_2O$ added per 100 moles of CO and $H_2$
*[3] Moles of $CH_4$ or $CO_2$ per 100 moles of CO converted Comparison of the data with and without the external $H_2O$ addition clearly establishes the advantages of $H_2O$ addition; (1) the CO conversion increases markedly (up to 2.5 fold increase), (2) the methane make is greatly reduced and, (3) the desired heavy hydrocarbon product yields, which may be gauged by the $C_{10}$+ selectivity, increase dramatically.

Thus, this example clearly demonstrates the benefits of conducting a Fischer-Tropsch hydrocarbon synthesis reaction with external $H_2O$ addition in the presence of a catalyst comprising metal cobalt.

Example 2

Another batch of a bulk cobalt catalyst was prepared using highly purified $Co(NO_3)_2 \cdot 6H_2O$ (99.99% pure Puratronic grade) according to a procedure similar to that described in Example 1. The evaluation procedure was also identical to that used in Example 1. After an extended reduction in a flowing $H_2$/He mixture at 500° C., the material was passivated and found to have about 1.5 m$^2$ surface area per gram. This catalyst (5 grams) and 10 grams of quartz powder were mixed and charged into the reactor and pretreated as described in Example 1. At 201.5° C. and 20.7 atm, a gas mixture composed of 63.1% $H_2$, 33.0% Co and 3.9% $N_2$ was passed at a rate of 105 Scm$^3$/m. After one day on stream the data in Table 2 were obtained.

TABLE 2

EFFECTS OF ADDED $H_2O$ ON THE ACTIVITY AND SELECTIVITIES OF CO HYDROGENATION OVER A HIGH-PURITY BULK Co CATALYST

Temperature = 202° C.
Feed Gas Composition = 63.1% $H_2$/33% CO/3.9% $N_2$
Pressure = 20 atm
SV = 1200 Scm$^3$/g hour

|  | Run 5 | Run 6 |
|---|---|---|
| % $H_2O$ Added | 0 | 21 |
| % CO Conversion | 7.2 | 15.6 |
| $CH_4$ Selectivity | 8.2 | 4.2 |
| 1-Olefin/Paraffin Ratio |  |  |
| $C_2$ | 0.13 | 0.36 |
| $C_3$ | 2.47 | 3.68 |
| $C_4$ | 1.87 | 2.52 |
| Hydrocarbon Product Distribution, wt. % |  |  |
| $CH_4$ | 9.4 | 4.8 |
| $C_2$-$C_4$ | 21.1 | 20.4 |
| $C_5$-$C_9$ | 11.0 | 11.6 |
| $C_{10}+$ | 58.5 | 63.2 |

Example 3

Using a test rig similar to that used above, a 12% cobalt on titania (rutile) catalyst was tested with and without water addition. The titania was Digussa p. 25, 50-150 mesh and the catalyst was prepared by depositing cobalt nitrate into the titania, drying in air, calcining, and reducing in flowing hydrogen.

The results are shown in Table 3.

TABLE 3

EFFECTS OF ADDED $H_2O$ ON THE ACTIVITY AND SELECTIVITY OF CO HYDROGENATION OVER 12% Co/$TiO_2$ CATALYST

Temperature = 200° C. ± 2° C.
Pressure = 20.7 atm
(catalyst diluted with rutile powder, 5 pt catalyst/6 pt powder)

| GHSV, cm$^3$/gm-hour | 3540 | 3540 | 1180 | 1180 |
|---|---|---|---|---|
| % $H_2O$ added based on $H_2$ + CO | 0 | 12 | 0 | 35 |
| Feed Gas Composition, Mol % |  |  |  |  |
| $H_2$ | 63.9 | 57.4 | 63.9 | 47.8 |
| CO | 32.1 | 28.9 | 32.1 | 24.0 |
| $N_2$ | 4.0 | 3.6 | 4.0 | 3.0 |
| $H_2O$ | 0 | 10.1 | 0 | 25.2 |
| % CO Conversion | 8.5 | 21.9 | 40.2 | 50.7 |
| % Selectivity |  |  |  |  |
| $CH_4$ | 9.6 | 4.1 | 6.5 | 2.7 |
| $CO_2$ | 0.22 | 0.21 | 0.15 | 0.68 |
| Olefin/Paraffin |  |  |  |  |
| $C_2$ | 0.20 | 0.78 | 0.11 | 0.47 |
| $C_3$ | 2.22 | 3.92 | 1.61 | 3.29 |
| $C_4$ | 1.24 | 2.38 | 0.84 | 2.00 |

The results of the test show clearly that water addition to a cobalt/titania catalyst increases catalyst activity by virtue of the CO conversion and methane make is significantly reduced. Also, $CO_2$ formation is virtually nonexistent, thereby showing that the KE reaction is also virtually nonexistent in these circumstances.

Table 4 shows the improved $C_5+$ selectivity obtained from the experiment of Example 3. Some of the data is repeated.

TABLE 4

EFFECT OF ADDED $H_2O$ ON ACTIVITY/SELECTIVITY OF 12% Co/$TiO_2$ CATALYST

Temperature = 200° C.
Pressure = 20 atm

| GHSV, SCM$^3$/gm-hour[1] | 3540 | 3540 | 1180 | 1180 |
|---|---|---|---|---|
| % $H_2O$ Added[2] | 0 | 12 | 0 | 35 |
| % CO Conversion | 8.5 | 21.9 | 40.2 | 50.7 |
| % $CH_4$ Selectivity[3] | 9.6 | 4.1 | 6.5 | 2.7 |
| % $CO_2$ Selectivity[3] | 0.22 | 0.21 | 0.15 | 0.68 |
| $CH_4$, Wt. % | 10.9 | 4.6 | 7.5 | 3.1 |
| $C_2$-$C_4$ | 9.8 | 5.0 | 8.1 | 4.7 |
| $C_5$-$C_9$ | 15.9 | 9.3 | 13.2 | 10.5 |
| $C_{10}+$ | 63.4 | 81.1 | 71.2 | 81.6 |
| $C_{10}$-$C_{20}$ |  | 21.0 |  | 24.9 |
| $C_{21}$-$C_{30}$ |  | 16.9 |  | 15.1 |
| $C_{31}$-$C_{40}$ |  | 13.1 |  | 9.5 |
| $C_{41}$-$C_{50}$ |  | 9.4 |  | 6.8 |
| $C_{50}+$ |  | 20.7 |  | 15.0 |

[1]cm$^3$ of $H_2$ = CO (1 atm, 22° C.) per gram of catalyst per hour
[2]moles $H_2O$ added per 100 moles of $H_2$ + CO
[3]moles $CH_4$ or $CO_2$ produced per 100 moles of CO converted The results conclusively show that water addition increases both activity and selectivity of the cobalt/titania catalyst, and that $CO_2$ remains quite low.

Example 4

Ruthenium Supported on Titania

A 1.1% Ru/$TiO_2$ catalyst was prepared by impregnating Degussa P-25 $TiO_2$ (sieved at 80-140 mesh; BET area=28 M$^2$/g; 70% rutile—30% anatase) with an acetone solution of Ru(NO$_3$)$_3$, drying at 120° C. and reducing at 450° C. in a $H_2$ flow (1 atm) for 5 hours. The catalyst thus prepared was passivated at room temperature and characterized to contain 1.1 wt. % Ru, and 70% of Tu was exposed to surface. 5.0 grams of Ru/$TiO_2$ and 10.0 grams of quartz powder (diluent; 80-140 mesh) were mixed thoroughly and charged in a down-flow fixed-bed reactor made of ⅜" OD stainless steel tube with a concentric ⅛" OD Thermocouple well.

The use of a diluent and an aluminum block jacket fitted tightly around the reactor minimized uneven temperature profile along the bed. The catalyst was then re-reduced in a flowing $H_2$ stream (200 cc/m, 1 atm) overnight at 450° C., cooled to 175° C. and then pressurized to 20.7 atm using a pre-mixed gas composed of 64% $H_2$, 32% CO and 4% $N_2$. At pressure and at a pre-set flow rate, the temperature was raised to 200° C. over a period of 2 hours and then data acquisition was initiated. The rate of CO conversion and the rates of formation of various products were monitored by use of two on-line GC's equipped with both TCD and FID. The data taken after 125 hours on-stream-time are shown in Table 5.

Comparison of the data in Runs 1, 2, and 3 shows clear benefits of performing external $H_2O$ addition; (1) the productivity increases nearly 3 fold when 22.4% $H_2O$ was added and (2) the hydrocarbon products become heavier (less undesirable $CH_4$ and more desirable $C_5+$ or $C_{10}+$ products). A similar trend was observed when the external $H_2O$ addition was carried out at a lower space velocity (Runs 4 and 5).

TABLE 5

EFFECTS OF EXTERNAL H₂O ADDITION ON ACTIVITY SELECTIVITIES OF 1.1% Ru/TiO₂ IN CO HYDROGENATION

Temperature = 200° C.
Pressure = 20.7 atm
Feed Gas Composition = 64% H₂/32% CO/4% N₂

|  | Run 1 | Run 2 | Run 3 | Run 4 | Run 5 |
|---|---|---|---|---|---|
| SV*¹, Scm³/g hr | 2460 | 2460 | 2460 | 1230 | 1230 |
| % H₂O added*² | 0 | 5.8 | 22.4 | 0 | 20.3 |
| % CO Converted | 6.3 | 10.4 | 17.2 | 17.9 | 35.2 |
| CH₄ Selectivity*³ | 5.8 | 3.1 | 1.6 | 3.9 | 1.5 |
| CO₂ Selectivity*³ | 0.34 | 0.45 | 0.42 | 0.50 | 0.60 |
| Hydrocarbon Product Distribution, wt. % | | | | | |
| CH₄ | 6.5 | 3.6 | 1.8 | 4.5 | 2.1 |
| C₂-C₄ | 12.6 | 7.4 | 4.1 | 9.6 | 4.8 |
| C₅-C₉ | 29.3 | 20.2 | 11.9 | 18.0 | 12.0 |
| C₁₀+ | 51.6 | 68.8 | 82.2 | 67.9 | 81.1 |
| C₅+ | 80.9 | 89.0 | 94.1 | 85.9 | 93.1 |

*¹cc of H₂ and CO measured at 1 atm., 22° C. per gram of catalyst per hour
*²Moles of H₂O added per 100 moles of CO and H₂
*³Moles of CH₄ or CO₂ produced per 100 moles of CO converted

Example 5

12% Co-0.5% Re/TiO₂

This example demonstrates the benefits of external H₂O addition when Fischer-Tropsch hydrocarbon synthesis reactions are carried out using promoted Co/TiO₂ catalysts. This example specifically shows that the benefits of external H₂O addition for Fischer-Tropsch synthesis over a Co/TiO₂ catalyst are not diminished by addition of a promoter, or promoters, to the base catalyst, Co/TiO₂ as exemplified by the beneficial effects of external water addition to a rhenium promoted Co/TiO₂ catalyst.

109 grams of Co(NO₃)₂.6H₂O and 16 cc of aqueous perrhenic acid containing 0.83 g of rhenium (as metal) were dissolved in 300 cc acetone, to which 160 g of TiO₂ (rutile, BET=13.6 m²/g, 80-140 mesh) was added. The acetone was then removed in a rotary evaporator, followed by further drying a 140° C. in a vacuum. The resulting material was calcined in air at 250° C. for 3 hours. 3 g of this catalyst was intimately mixed with 12 g of diluent (low-surface-area rutile, 80-140 mesh) and charged to the reactor. The catalyst was then reduced in-situ in flowing H₂ (1 atm, 200 cc/m) by gradually raising the temperature from room temperature to 450° C. over a period of 4 hours and then keeping at 450° C. for 16 hours. The performance data, listed in Table 6, were taken after 200 hours on-stream-time.

TABLE 6

EFFECTS OF ADDED H₂O ON ACTIVITY AND SELECTIVITIES OF CO HYDROGENATION OVER RHENIUM PROMOTED Co/TiO₂ (12% Co-0.5% Re/TiO₂)

Total Pressure = 20.7 atm
Feed Gas Composition = 64% H₂/32% CO/4% N₂
Temperature = 200° C.

|  | Run 5 | Run 6 | Run 7 | Run 8 | Run 9 |
|---|---|---|---|---|---|
| SV, SCM³/g. hr | 3510 | 3510 | 3510 | 2340 | 2340 |
| % H₂O added | 0 | 12 | 26 | 0 | 18 |
| % CO Conversion | 9.9 | 24.2 | 26.4 | 21.0 | 36.3 |
| CH₄ Selectivity | 9.4 | 4.3 | 3.4 | 8.1 | 3.6 |
| CO₂ Selectivity | 0.39 | 0.38 |  | 0.27 | 0.38 |
| 1-Olefin/Paraffin Ratios | | | | | |
| C₂ | 0.34 | 0.48 | 0.63 | 0.22 | 0.56 |
| C₃ | 2.42 | 3.16 | 3.34 | 2.22 | 3.26 |
| C₄ | 1.71 | 1.97 | 2.39 | 1.24 | 1.97 |
| Hydrocarbon Product Distribution, wt. % | | | | | |
| CH₄ | 10.7 | 4.9 | 3.9 | 8.8 | 4.3 |
| C₂-C₄ | 8.4 | 4.2 | 3.6 | 5.9 | 4.0 |
| C₅-C₉ | 15.0 | 8.9 | 7.5 | 10.3 | 7.9 |
| C₁₀+ | 65.9 | 82.0 | 85.0 | 75.0 | 83.8 |
| C₅+ | 80.9 | 90.9 | 92.5 | 85.3 | 91.7 |

The results in Table 6 clearly establish that the benefits of external H₂O additions on the activity/selectivities of a rhenium-promoted Co/TiO₂ catalyst. This example thus establishes that promoted Co/TiO₂ catalysts show higher productivity and better product selectivities when external H₂O addition is performed during the Fischer-Tropsch hydrocarbon synthesis reaction.

Example 6

A series of runs to examine the influences of process variables, including the levels of externally added H₂O, were conducted using the catalyst and procedure described in Example 5, except that the catalyst used in this example was about 25% less active than that described in Example 5 due to different histories. The results in Table 7 nevertheless demonstrate that the beneficial effects of external H₂O addition can be realized both at a relatively low addition level of 6.7% and at a very high level of 104 %. Thus, this example demonstrates that for a wide range of external H₂O addition levels, 2-100% based on the combined H₂ and CO feeds, beneficial effects of increased productivity and desirable selectivities can be realized. The results in Table 7 also demonstrate that the beneficial effects of added H₂O do not vary significantly over the temperature ranges of 180°-220° C., which suggests that the effects of external H₂O addition do not vary significantly with process conditions.

TABLE 7

EFFECTS OF ADDED H₂O ON ACTIVITY AND SELECTIVITIES OF CO HYDROGENATION OVER RHENIUM PROMOTED Co/TiO₂

Sum of Partial Pressures of CO and H₂ = 20.0 atm
Feed Gas Composition = 64.2% H₂/31.8% CO/4.0% N₂

| Run # | SV SCM³/g. hr | Temperature °C. | % H₂O Added | % CO Conversion | CH₄ Selectivity |
|---|---|---|---|---|---|
| 10 | 3650 | 200 | 0 | 5.2 | 13.0 |
| 11 | 3650 | 200 | 6.7 | 13.7 | 5.8 |
| 12 | 3650 | 200 | 28.0 | 18.8 | 4.1 |
| 13 | 3650 | 200 | 34.0 | 15.8 | 3.3 |
| 14 | 3650 | 200 | 104.0 | 7.7 | 2.9 |
| 15 | 10950 | 221 | 0 | 5.7 | 16.2 |
| 16 | 10950 | 221 | 25.5 | 13.9 | 7.4 |
| 17 | 1210 | 181 | 0 | 8.2 | 9.0 |
| 18 | 1210 | 181 | 23.5 | 25.4 | 2.2 |

What is claimed:

1. A once-through, fixed or slurry bed Fischer Tropsch process with enhanced CO conversion activity and C₅+ liquid hydrocarbon selectivity comprising contacting a feed mixture of carbon monoxide and hydrogen in a reaction zone with about 1 Vol % to about 70 Vol % water based on the total volume of feed mixture, at a pressure above one atmosphere and a temperature ranging from about 150° C. to about 300° C., with a catalyst selected from the group consisting of cobalt, ruthenium, and mixtures thereof on a titania support, wherein said titania support is less than 40 m²/g, converting at least 90 Vol % of the carbon monoxide to liquid hydrocarbons, and in the substantial absence of $CO_2$ formation.

2. The process of claim 1 wherein the said catalyst is promoted with one or more promoter metals when said catalyst is a cobalt catalyst.

3. The process of claim 2 wherein said promoter metal is selected from the group consisting of Re, Hf and mixtures thereof.

4. The process of claim 3 wherein said catalyst contains rhenium promoter metal.

5. The process of claim 1 wherein the mole ratio of $H_2$ to CO in the feed ranges from about 0.5 to 6.

6. The process of claim 2 wherein the amount of cobalt catalyst ranges from about 2 wt % to about 25 wt % based on the total catalyst weight.

7. The process of claim 1 wherein the amount of ruthenium ranges from about 0.1 to 20 wt % ruthenium metal based on the total catalyst weight.

8. The process of claim 4 wherein the rhenium to cobalt ratio in said catalyst composition is greater than about 0.01 to 1.

9. The process of claim 2 wherein the $CH_4$ selectivity is less than about 10%.

10. The process of claim 1 wherein the $CO_2$ produced in the process is less than about 2% based on feed.

* * * * *